United States Patent [19]

Suzuki et al.

[11] Patent Number: 4,977,284

[45] Date of Patent: Dec. 11, 1990

[54] PROCESS FOR PRODUCING 1,4-BUTANEDIOL AND TETRAHYDROFURAN

[75] Inventors: Sadakatsu Suzuki; Hiroyuki Inagaki; Hiroshi Ueno, all of Saitama, Japan

[73] Assignee: Tonen Corporation, Tokyo, Japan

[21] Appl. No.: 450,104

[22] Filed: Dec. 13, 1989

[30] Foreign Application Priority Data

Dec. 14, 1988 [JP] Japan .................................. 63-313760

[51] Int. Cl.$^5$ ..................... C07D 307/08; C07C 27/06
[52] U.S. Cl. .................................... 549/508; 568/864; 568/885
[58] Field of Search ................. 549/508; 568/864, 885

[56] References Cited

U.S. PATENT DOCUMENTS

| | | | |
|---|---|---|---|
| 4,584,419 | 4/1986 | Sharif et al. ......................... | 568/864 |
| 4,652,685 | 3/1987 | Cawse et al. ......................... | 568/864 |
| 4,656,297 | 4/1987 | Kouba et al. ......................... | 549/508 |
| 4,751,334 | 6/1988 | McKee ................................ | 568/864 |

FOREIGN PATENT DOCUMENTS

| | | |
|---|---|---|
| 32567 | 12/1969 | Japan . |
| 23294 | 6/1972 | Japan . |
| 111975 | 5/1987 | Japan . |
| 25434 | 1/1990 | Japan . |
| 93151 | 10/1972 | United Kingdom . |
| 51741 | 8/1979 | United Kingdom . |

*Primary Examiner*—Richard L. Raymond
*Attorney, Agent, or Firm*—E. F. Sherer

[57] ABSTRACT

A process of producing 1,4-butanediol and tetrahydrofuran by catalytically hydrogenating maleic acid anhydride and/or succinic acid anhydride in a gas phase and in the presence of a catalyst.

5 Claims, No Drawings

PROCESS FOR PRODUCING 1,4-BUTANEDIOL AND TETRAHYDROFURAN

BACKGROUND OF THE INVENTION

The present invention concerns a process for producing 1,4-butanediol and tetrahydrofuran and, more in particular, it relates to a process for producing 1,4-butanediol and tetrahydrofuran, in which maleic acid anhydride and/or succinic acid anhydride are catalytically hydrogenated in a gas phase under the presence of a catalyst.

PRIOR ART 1,4-butanediol is a compound useful as starting material for polybutylene terephthalate resin, polyurethane resin, etc. Accordingly, there is a need for a process for producing 1,4-butanediol at reduced cost and increased efficiency.

The following processes for producing γ-butyrolactone or 1,4-butanediol by catalytic hydrogenation of maleic acid anhydride and/or succinic acid anhydride or derivatives thereof have been disclosed.
(i) A process for producing γ-butyrolactone in which maleic acid anhydride or succinic acid anhydride, etc. are catalytically hydrogenated in a gas phase by using a catalyst comprising zinc-copper-chromium (Japanese Patent Publication Sho No. 44-32567).
(ii) A process for producing γ-butyrolactone in which maleic acid anhydride and/or succinic acid anhydride, etc. are catalytically hydrogenated in a gas phase under the presence of a reduction catalyst comprising copper oxide-beryllium oxide-zinc oxide (Japanese Patent Publication Sho No. 47-23294).
(iii) A process for producing 1,4-butanediol in which maleic acid anhydride and/or succinic acid anhydride, etc. are hydrogenated in a liquid phase under the presence of a catalyst containing elements belonging to sub-VII and sub-VIII groups or compounds thereof (Japanese Patent Laid-Open Sho No. 51-133212).
(iv) A process for producing 1,4-butanediol in which maleic acid diester or fumaric acid diester, etc. are hydrogenatively decomposed in a gas phase under the presence of a copper chromite catalyst (Japanese Patent Laid-Open Sho No. 61-22035, Japanese Patent Published Publication Sho No. 62-501702).

Further, the inventors of the present invention have proposed a process for producing 1,4-butanediol by catalytically hydrogenating maleic acid anhydride and/or succinic acid anhydride in a gas phase under the presence of a copper oxide-zinc oxide catalyst (Japanese Patent Application No. Sho 63-175062).

Tetrahydrofuran is also a compound useful as the starting material for polytetramethylene glycol, etc., or a solvent for polyvinyl chloride or polyurethane, and thus, there is a need for a process for producing tetrahydrofuran, which is inexpensive and efficient.

The following process for producing tetrahydrofuran by catalytic hydrogenation of maleic acid anhydride and/or succinic acid anhydride have been disclosed.
(i) A process for producing tetrahydrofuran by hydrogenating and dehydrating maleic acid anhydride and/or succinic acid anhydride and/or γ-butyrolactone in a gas phase under the presence of a mixed catalyst of a copper series catalyst and a dehydrating catalyst (Japanese Patent Publication Sho No. 48-30272).
(ii) A process for producing γ-butyrolactone and/or tetrahydrofuran by hydrogenating maleic acid anhydride and/or succinic acid anhydride in a liquid phase under the presence of a solid catalyst comprising palladium, cobalt and niobium (Japanese Patent Laid-Open Sho No. 62-111975).

The processes for producing 1,4-butanediol, which are disclosed above, have a number of problems. For instance, in the process for catalytically hydrogenating maleic acid anhydride and/or succinic acid anhydride in a gas phase under the presence of a catalyst, there has been a problem that only γ-butyrolactone can be formed instead of 1,4-butanediol, except for the process proposed above by the present inventors. Further, the method of hydrogenating maleic acid anhydride and/or maleic acid in a liquid phase under the presence of a catalyst has a problem of requiring a high pressure of about 200 kg/cm$^2$ and, thus require an enormous installation cost and running cost. Although, a process of hydrogenatively decomposing maleic acid diester, etc. in a gas phase under the presence of a catalyst does not require the high pressure described above, it does require a step of diesterifying maleic acid anhydride, which makes the process extremely complicated. That is, since the reaction of converting a monoester into a diester is a equilibrium reaction, two reaction steps are required for sufficiently completing the reaction and it is necessary to add three reaction steps including the mono-esterifying step.

On the other hand, the production processes for tetrahydrofuran as disclosed above have a number of problems. For instance, in the process for producing tetrahydrofuran from maleic acid anhydride, etc. under the presence of a mixed catalyst of a copper series and a dehydrating catalyst, it is required that hydrogenation and dehydration are conducted in respective reaction zones divided into three regions and, accordingly, the reaction apparatus is complicated and the process is also complicated. Further, the process of using a catalyst comprising palladium, cobalt and niobium requires high pressure for conducting hydrogenating reaction in a liquid phase and large amounts of γ-butyrolactone are produced as by-products.

Further, a process for producing 1,4-butanediol and tetrahydrofuran together by catalytic hydrogenation of maleic acid anhydride and/or succinic acid anhydride in a gas phase has not yet been known.

The present invention overcomes or at least mitigates the above described problems of requiring high installation cost and running cost and using a complicated process upon producing 1,4-butanediol and tetrahydrofuran from maleic acid anhydride and/or succinic acid anhydride.

DESCRIPTION OF THE INVENTION

The present inventors have considered that it will be beneficial if maleic acid anhydride and/or succinic acid anhydride are hydrogenated directly at a reduced pressure thereby producing 1,4-butanediol and tetrahydrofuran and have made various studies on gas phase hydrogenation processes.

It has also been considered that the γ-butyrolactone can only be obtained in the gas phase hydrogenation of maleic acid anhydride and/or succinic acid anhydride, because the reaction is conducted at a low hydrogen/starting material ratio and at a pressure near the normal pressure in each of the cases. Then, when hydrogenating reaction has been carried out at a higher hydrogen/- starting material ratio than usual and under an elevated pressure within such a range that the gas phase can be maintained, it has been found that 1,4-butanediol and tetrahydrofuran can be produced together at high yield and the present invention has been accomplished based on such a finding.

That is, the present invention concerns a process for producing 1,4-butanediol and tetrahydrofuran, wherein maleic acid anhydride and/or succinic acid anhydride are catalytically hydrogenated in a gas phase under the presence of a solid catalyst containing copper, chromium and manganese.

Catalyst

The catalyst used in the present invention is usually a previously reduced copper oxide-chromium oxide-manganese oxide catalyst. Such a catalyst is prepared, for example, by dropping an aqueous solution of sodium carbonate at about 90° C. into an aqueous solution of copper nitrate and manganese nitrate, mixing them adding chromium oxide, stirring sufficiently, recoverying by filtration and, after drying and pulverization step, molding them into a predetermined shape by using a molding machine. In this preparation method, a catalyst with support can be obtained in which copper oxide and manganese oxide are supported on chromium oxide.

Reduction of the catalyst in the present invention is carried out, for example, by passing a nitrogen gas containing 2 vol % of hydrogen to a catalyst at a gas space velocity converted into that at normal temperature and normal pressure (hereinafter simply referred to as G.H.S.V., which shows a value for normal temperature and normal pressure in each of the cases) at about 2,400 hr$^{-1}$ and a pressure of several tons of kg/cm$^2$G at 170° C. for one day and one night, further gradually increasing the hydrogen concentration to 100 vol % and then passing the gas for several hours at a temperature of the catalyst bed of 200° C.

Solvent

Although there is no particular restrictions for the solvent usable in the present invention, γ-butyrolactone, tetrahydrofuran, dimethyl ether, diethyl ether and 1,4-dioxane may be used for example. Among them, γ-butyrolactone is particularly preferred since it is a good solvent for maleic acid anhydride and succinic acid anhydride, one of hydrogenation products and considered to be an intermediate product of 1,4-butanediol. The solvent does not need to be used.

Catalytic Condition

Catalytic contact between a gas mixture of maleic acid anhydride and/or succinic acid anhydride and a hydrogen, and a catalyst can properly be selected from the methods known so far. For instance, such methods include contacting the gas mixture and the catalyst in a fixed bed system, a method of contacting them in a moving bed system or a method of contacting them in a fluidized bed system. Depending on a case, the gas mixture and the catalyst can be brought into contact batchwise.

The time of contact between the gas mixture of maleic acid anhydride and/or succinic acid anhydride and hydrogen, and the catalyst is from 1,000 to 100,000 hr$^{-1}$, preferably, about 4,000 to 20,000 hr$^{-1}$ expressed as G.H.S.V.

The reaction temperature in the present invention is about 180° to 280° C., the reaction pressure is about 10 to 100 kg/cm$^2$G and the molar ratio of hydrogen gas to maleic acid anhydride and/or succinic acid anhydride is about from 100 to 1,500. The reaction temperature, the reaction pressure and the hydrogen gas/starting material molar ratio are property selected within such a range as capable of maintaining the gas phase.

However, if the hydrogen gas/starting material molar ratio is below 100, it tends to cause reduction in the reaction rate and catalyst degradation due to the information of carbonaceous substance. On the other hand, if it exceeds 1,500, since a great amount of hydrogen has to be recycled, it is disadvantageous from an economical point of view.

The production ratio of 1,4-butanediol and tetrahydrofuran in the products according to the present invention, which will differ depending on the reaction pressure and the reaction temperature, is generally within a range of: tetrahydrofuran/1,4-butanediol = 1/20 to 9/1 in molar ratio.

1,4-butanediol and tetrahydrofuran in the reaction mixture after the completion of the reaction can easily be separated by means of a known method, for example, distillation.

By the process according to the present invention, it is possible to obtain 1,4-butanediol and tetrahydrofuran from maleic acid anhydride and/or succinic acid anhydride in one step reaction at a high yield, as well to remarkably simplify the production process. In addition, as compared with hydrogenation in liquid phase, since 1,4-butanediol and tetrahydrofuran can be produced at a remarkably lower pressure, this will result in a reduction of installation cost and running cost.

The present invention will now be described referring to examples but the invention is not restricted only to these examples.

EXAMPLE 1

A commercially available copper chromium series oxide catalyst (trade name: G-89, manufactured by Nissan Gardler Co.) comprising copper, chromium and manganese by 38.9% by weight, 37.3% by weight and 3.6% by weight respectively was charged by 15 cc into a fixed bed reactor (15 mm × 600 mm) and pressurized in a nitrogen gas stream to 40 kg/cm$^2$G and heated to 170° C. Subsequently, hydrogen was gradually added to the nitrogen gas stream and nitrogen gas containing 2 vol % of hydrogen was caused to pass under 40 kg/cm$^2$G, at 170° C., and G.H.S.V. of 2,400 hr$^{-1}$ over one night. Then, hydrogen concentration was gradually increased up to 100% by volume hydrogen while taking care such that the catalyst bed temperature did not exceed 200° C., and reduction was conducted under 40 kg/cm$^2$G, at 200° C. and at G.H.S.V. of 2,400 hr$^{-1}$ for 2 hours.

After heating the fixed bed reactor to 180° C., a solution of maleic acid anhydride in γ-butyrolactone (maleic acid anhydride/γ-butyrolactone = 1/1 molar ratio) and hydrogen were caused to pass at a ratio of 200 mol of hydrogen based on one mol of the sum of maleic acid anhydride and γ-butyrolactone under an elevated pressure of 40 kg/cm$^2$G and under the conditions of G.H.S.V. of 9,000 hr$^{-1}$. The product was analyzed by gas chromatography and the product was identified by GC-MS.

As a result, conversion of maleic acid anhydride was 100 mol %, and 60.5 mol % of 1,4-butanediol, 11.3% mol of tetrahydrofuran and 1.0 mol % of n-butanol were formed based on maleic acid anhydride supplied. In addition, a slight amount of n-propanol was also formed but succinic acid anhydride was not detected in the product.

EXAMPLE 2

The catalyst reduction treatment and the reaction were conducted in the same procedures as those in Example 1 except for changing the pressure upon catalyst reduction and the reaction pressure to 15 kg/cm$^2$G and the reaction temperature to 210° C. and changing the molar ratio of maleic acid anhydride to γ-butyrolactone to 1/3.

As a result, the conversion of maleic acid anhydride was 100 mol %, and 38.0 mol % of 1,4-butanediol, 51.5 mol % of tetrahydrofuran and 6.5 mol % of n-butanol were formed based on maleic acid anhydride supplied. Succinic acid anhydride was not detected in the product.

EXAMPLE 3

The catalyst reduction treatment and the reaction were conducted in the same procedures as those in Example 2 except for replacing maleic acid anhydride with succinic acid anhydride and changing the reaction temperature to 200° C. and the molar ratio of succinic acid anhydride to γ-butyrolactone to ¼.

As a result, the conversion of the succinic acid anhydride was 100 mol %, and 1,4-butanediol was formed at a yield of 41.1 mol % and tetrahydrofuran was formed at a yield of 55.7 mol % based on succinic acid anhydride supplied.

EXAMPLE 4

Into 0.4 liter of an aqueous solution containing 0.4 mol copper nitrate and 0.04 mol of manganese nitrate at 90° C., under stirring, and aqueous solution of sodium carbonate of 1 mol/liter was dropped till pH was adjusted to 7.0. Further, 34 g of chromium oxide (III) was added, to the above-mentioned aqueous solution and stirred for 2 hours while maintaining the temperature at 90° C. After allowing them to cool, the resultant solid was separated by filtration and washed with 5 liter of warmed water at 60° C. Then, it was dried for 12 hours while supplying air at 140° C. and then further baked at 350° C. for 3 hours. After pulverizing the thus sintered solid, 10–20 mesh fractions were sieved to obtain a solid catalyst comprising, copper, chromium and manganese. The content of copper, chromium and manganese as the metal component in the resultant catalyst was 36% by weight, 34% by weight and 3% by weight respectively.

Using 10 cc of the catalyst prepared as described above, the catalyst reduction treatment and reaction were carried out in the same procedures as those in Example 1.

As a result, the conversion of maleic acid anhydride was 100 mol %, and 49.8 mol % of 1,4-butanediol, 8.6 mol % of tetrahydrofuran and 0.7 mol % of n-butanol were formed based on maleic acid anhydride supplied. Succinic acid anhydride was not detected in the product.

EXAMPLE 5

Using the reduction catalyst employed in Example 4, a gas mixture of maleic acid anhydride and hydrogen (1:600 molar ratio) was caused to pass without using solvent under the condition at 220° C., under 40 kg/cm$^2$G and at G.H.S.V. of 4,800 hr$^{-1}$.

As a result, the conversion of maleic acid anhydride was 100 mol %, and 73.5 mol % of 1,4-butanediol and 14.7 mol % of tetrahydrofuran were formed based on maleic acid anhydride supplied. Succinic acid anhydride was not detected in the product.

EXAMPLE 6

Using the reduction catalyst employed in Example 4, a solution of maleic acid anhydride in 1,4-dioxane (maleic acid anhydride/¼-dioxane=¼ molar ratio) and hydrogen were caused to pass at a ratio of 800 mol of hydrogen based on one mol of maleic acid anhydride under the conditions at 220° C., under an elevated pressure of 60 kg/cm$^2$G and at G.H.S.V. of 4,800 hr$^{-1}$.

As a result, the conversion of maleic acid anhydride was 100 mol %, and 80.4 mol % of 1,4-butanediol and 10.5 mol % of tetrahydrofuran were formed based on maleic acid anhydride supplied. Succinic acid anhydride was not detected in the product.

COMPARATIVE EXAMPLE 1

Catalyst reduction treatment and reaction were conducted in the same procedures as those in Example 1 except for using 15 cc of a commercially available copper chromium oxide catalyst containing copper and chromium by 40.0% by weight and 26.5% by weight respectively as the metal components (G-13: trade name of products manufactured by Nissan Gardler Co.).

As a result, the conversion of maleic acid anhydride was 100 mol %, and while 1,4-butanediol was formed by 50.2 mol % based on maleic acid anhydride supplied but tetrahydrofuran was scarcely formed, that is, at 0.4 mol %. Other products were 0.7 mol % of n-butanol, etc. but succinic acid anhydride was not detected in the product.

COMPARATIVE EXAMPLE 2

A manganese oxide-chromium oxide catalyst was prepared in the same procedures as those in Example 4 except for not adding a compound containing the copper ingredient.

Using 15 cc of the catalyst prepared as above, when catalyst reducing treatment and reaction were conducted in the same procedures as those in Example 1, the conversion of maleic acid anhydride was 2 mol % 1,4-butanediol and tetrahydrofuran were not detected in the product.

What is claimed is:

1. A process of producing 1,4-butadienol and tetrahydrofuran comprising:
    hydrogenating a compound selected from group consisting of maleic acid anhydride, succinic acid anhydride, and mixtures thereof in a gas phase and in the presence of a catalyst comprising copper, chromium, and manganese.
2. The process recited in claim 1 wherein said catalyst is reduced copper oxide, chromium oxide, and manganese oxide.
3. The process recited in claim 2 wherein said compound is contained in a solvent.
4. The process recited in claim 3 wherein said compound is maleic acid anhydride.
5. The process recited in claim 4 wherein tetrahydrofuran and 1,4-butanediol is produced in a molar ratio of from about 1/20 to 9/1.

* * * * *